US00PP27510P3

(12) United States Plant Patent
Yamada

(10) Patent No.: US PP27,510 P3
(45) Date of Patent: Dec. 27, 2016

(54) ***PETUNIA* PLANT NAMED 'SUNPETU 101'**

(50) Latin Name: *Petunia×hybrida*
Varietal Denomination: Sunpetu 101

(71) Applicant: SUNTORY FLOWERS LIMITED, Tokyo (JP)

(72) Inventor: Masahiro Yamada, Kanagawa (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 73 days.

(21) Appl. No.: 14/121,578

(22) Filed: Sep. 19, 2014

(65) Prior Publication Data

US 2015/0089702 P1 Mar. 26, 2015

Related U.S. Application Data

(60) Provisional application No. 61/960,556, filed on Sep. 20, 2013.

(51) Int. Cl.
*A01H 5/02* (2006.01)

(52) U.S. Cl.
USPC ..... Plt./356.13
CPC ..... *A01H 5/02* (2013.01)

(58) Field of Classification Search
USPC ..... Plt./356.13
See application file for complete search history.

(56) References Cited

U.S. PATENT DOCUMENTS

2014/0215669 P1 7/2014 Tsukahara

OTHER PUBLICATIONS

"2012 Spring-Summer gardening catalog," Daiichi Engei Co., Ltd., Oct. 2011, pp. 8-9.
Registration No. 22221, Registration date Jan. 28, 2013, Suntory Flowers Company, 1 page.

*Primary Examiner* — June Hwu
(74) *Attorney, Agent, or Firm* — Kilpatrick Townsend & Stockton LLP

(57) ABSTRACT

Disclosed herein is a new and distinct variety of *Petunia* plant having vigorous and semi-trailing habit, abundant flowering, the whole bush remaining in bloom for a considerable period of time, and single, medium sized and vivid purple-white bicolored flowers.

2 Drawing Sheets

Botanical designation: *Petunia×hybrida.*
Cultivar denomination: 'Sunpetu 101'.

BACKGROUND OF THE INVENTION

The present invention relates to a new and distinct variety of *Petunia* plant, which is hereinafter referred to as 'Sunpetu 101'.

A *Petunia* is a very popular plant that is used in flower bedding and potting in the summer season.

This purpose of this invention is to obtain a new *Petunia* cultivar with vigorous and semi-trailing habit, abundant flowering, the whole bush remaining in bloom for a considerable period of time, and single, medium sized and vivid purple-white bicolored flowers.

The new *Petunia* plant originated from cross-pollination of the female parent 'P23F1-8' and the male parent 'MP22-188-2'. The female parent 'P23F1-8' (unpatented) used in the crossing of 'Sunpetu 101' is a strain of the applicant's breeding lines (i.e., proprietary *Petunia* selection), having medium plant diameter, and the male parent 'MP22-188-2' (unpatented) used in the crossing of 'Sunpetu 101' is a strain of the applicant's breeding lines (i.e., proprietary *Petunia* selection), having purple petals. The cross-pollination was conducted in Sep. 10, 2010 at Yame-gun, Fukuoka, Japan.

In March 2011, the seedlings obtained by the crossing were planted in a field. In May 2011, some seedlings were selected in view of growth habit, flower size and color thereof. Shortly thereafter stem tip culturing was carried out, and then the propagation was started.

In November 2012, the cultivation of the seedlings was repeated. The botanical characteristics of that plant were then examined, using similar varieties 'Daiichi-MP22-193-1' and 'Daiichi-MP22-21-2' for comparison. As a result, it was concluded that this *Petunia* plant is distinguishable from any other variety, whose existence is known, and is uniform and stable in its characteristics.

The new variety of *Petunia* plant was then named 'Sunpetu 101'.

SUMMARY OF THE INVENTION

This new variety is unlike any *Petunia* commercially available as evidenced by the following unique combinations of characteristics.

1. Vigorous and semi-trailing habit.
2. Abundant flowering, the whole bush remaining in bloom for a considerable period of time.
3. Single, medium sized and vivid purple-white bicolored flowers.

The new variety 'Sunpetu 101' differs from the similar variety 'Daiichi-MP22-193-1', which was applied for Japanese plant variety protection (the application number: 27366; the application date: 2012 Sep. 3; the registration number 23231; the registration date: 2014 Mar. 10), in the following points.

1. The plant height of 'Sunpetu 101' is medium. That of 'Daiichi-MP22-193-1' is low.
2. The main color of surface of corolla lobe of 'Sunpetu 101' is vivid purple (RHS N81A) and white (RHS NN155C). That of 'MP22-193-1' is PURPLE-VIOLET (RHS N81).

The new variety 'Sunpetu 101' differs from the similar variety 'Daiichi-MP22-21-2', which was applied for Japanese plant variety protection (the application number: 26284; the application date: 2011 Sep. 8; the registration number 22221; the registration date: 2013 Jan. 28), in the following points.

1. The plant height of 'Sunpetu 101' is medium. That of 'Daiichi-MP22-21-2' is somewhat low.
2. The flower diameter of 'Sunpetu 101' is medium (about 4.8 cm). That of 'Daiichi-MP22-21-2' is somewhat small.
3. The main color of surface of corolla lobe of 'Sunpetu 101' is vivid purple (RHS N81A) and white (RHS NN155C). That of 'Daiichi-MP22-21-2' is RED-PURPLE (RHS N74).

This new variety of *Petunia* plant 'Sunpetu 101' was asexually reproduced by the use of cuttings in Higashiomi, Shiga, Japan, and homogeneity and stability thereof were confirmed. A cutting used to reproduce the new variety typically has one or more leaves and a stem. The instant plant retains its distinctive characteristics and produces true to type in successive generations.

BRIEF DESCRIPTION OF THE PHOTOGRAPHS

The depicted plants had been reproduced by the use of cuttings and were photographed during October 2013 while growing outdoors in wall pots with about 24 cm of container size at an age of approximately 5 months.

FIG. 1 is a photograph of a typical plant of the new variety of *Petunia* plant 'Sunpetu 101' while growing in a pot.

FIG. 2 is a photograph of a close view of flowers of the new variety of *Petunia* plant 'Sunpetu 101'.

DETAILED BOTANICAL DESCRIPTION

In October 2013, the cultivation of the seedlings was repeated at Higashiomi, Shiga, Japan. The average day temperature was about 23° C., and the average night temperature was about 13° C. The plants were grown under natural sunlight. The number of days to flowering (response time) was 2-3 weeks. The quality was maintained for about 150 days. The plants had temperature resistance to about −5° C. (the lowest temperature) and about 35° C. (the highest temperature). Further, the plants had good tolerance to pests and pathogens.

For the parentage information: The female parent 'P23F1-8' (unpatented) used in the crossing of 'Sunpetu 101' is a strain of the applicant's breeding lines (i.e., proprietary selection of *Petunia×hybrida*), having medium plant diameter, and the male parent 'MP22-188-2' (unpatented) used in the crossing of 'Sunpetu 101' is a strain of the applicant's breeding lines (i.e., proprietary selection of *Petunia×hybrida*), having purple petals.

For the propagation information: approximate soil and/or air temperature was around 15-20° C.; the new cultivar was propagated by cutting; number of days to initiate roots was about 7 days; number of days to produce a rooted young plant was about 21 days; free-root branching; root color was white; and root texture was fibrous.

The botanical characteristics of the new and distinct variety of *Petunia* plant named 'Sunpetu 101' at an age of approximately 5 months are shown in the following TABLE 1. In the following description, the color-coding is in accordance with the Horticultural Colour Chart of The Royal Horticultural Society, London, England (R.H.S. Colour Chart The 5th edition 2007).

TABLE 1

PLANT VARIETY DESCRIPTION

| CHARACTERISTIC | APPLICATION VARIETY Sunpetu 101 |
|---|---|
| ANNUAL, BIENNIAL or PERENNIAL? | Grown as annual |
| TYPE OF PLANT: i.e., TREE, SHRUB, SUBSHRUB, VINE, CUT FLOWER, POTTED PLANT | Potted plant |
| APPROPRIATE CONTAINERS +/or CROPPING SYSTEM | Ideal for pots, hanging baskets or planters, and is good for use as a ground cover. |
| GROWTH HABIT | Semi-trailing |
| PLANT HEIGHT | About 25.0, Medium cm |
| PLANT DIAMETER OR AREA OF SPREAD | About 60.0 cm |
| PLANT VIGOR | Vigorous |
| BRANCHING HABIT | Freely branching |
| BASAL BRANCHING? | Present |
| PINCHING REQUIRED? | Required |
| NUMBER OF LATERAL BRANCHES | Many |
| LATERAL BRANCH LENGTH | About 24.3 mm |
| LATERAL BRANCH DIAMETER | About 1.4 mm |
| INTERNODE LENGTH OF A STEM | About 17.3 mm |
| STEM ASPECT | Upright to outward |
| STEM COLOR (and bark color, if applicable) | Near 143B RHS |
| STEM PUBESCENCE? | Pubescent |
| OTHER PLANT/STEM CHARACTERISTICS | — |
| LEAF ARRANGEMENT | Alternate |
| COMPOUND OR SIMPLE? | Simple |
| QUANTITY OF LEAVES PER LATERAL BRANCH | Many |
| LEAF SHAPE | Elliptic |
| LEAF TIP | Acute |
| LEAF BASE | Cuneate |
| LEAF LENGTH | About 41.3 mm |
| LEAF WIDTH | About 14.8 mm |
| LEAF THICKNESS | About 0.3 mm |
| LEAF PUBESCENCE? WHICH SIDE? | Pubescent, both sides |
| LEAF MARGIN | Entire |
| VENATION PATTERN | Pinnate |
| LEAF COLOR, YOUNG, UPPER SIDE | Near 137B RHS |
| LEAF COLOR, YOUNG, UNDER SIDE | Near 137D RHS |
| LEAF COLOR, MATURE, UPPER SIDE | Near 137A RHS |
| LEAF COLOR, MATURE, UNDER SIDE | Near 137C RHS |
| VENATION COLOR, UPPER SIDE | Near 144C RHS 145A (Yellow Green |
| VENATION COLOR, UNDER SIDE | Near 144D RHS 145A (Yellow Green |
| PETIOLE LENGTH | About 3.3 mm |
| PETIOLE DIAMETER | About 1.8 mm |
| PETIOLE TEXTURE | Pubescent, dense, long |
| PETIOLE COLOR | Near 144C RHS |
| STIPULES, TENDRILS, THORNS, SPINES OR PRICKLES? IF SO, GIVE COLOR AND SIZE | — |
| OTHER FOLIAGE CHARACTERISTICS | — |
| FLOWER ARRANGEMENT | Borne in upper leaf axils |
| INFLORESCENCE TYPE OR FORM (if applicable) | Flower solitary |
| FLOWER TYPE or FORM | Single |
| FLOWERING HABIT | Continuously |
| QUANTITY OF FLOWERS PER LATERAL STEM | About 2 to 4 |

TABLE 1-continued

| PLANT VARIETY DESCRIPTION | |
|---|---|
| CHARACTERISTIC | APPLICATION VARIETY Sunpetu 101 |
| QUANTITY OF FLOWERS PER PLANT | About 64 |
| NATURAL FLOWERING SEASON | About Spring to late Autumn |
| TIME TO FLOWER OR RESPONSE TIME | About 2-3 weeks |
| FRAGRANCE | Absent |
| FLOWER BUD LENGTH | About 32.2 mm |
| FLOWER BUD DIAMETER | About 6.7 mm |
| FLOWER BUD SHAPE | Cylindrical with 5 lines, Tip: twisted |
| FLOWER BUD COLOR | Near 149D, Tip: RHS N82A-N82B |
| FLOWER ASPECT; i.e., UPRIGHT, OUTWARD, DROOPING, etc. | Upright to outward |
| FLOWER SHAPE | Salverform |
| FLOWER DIAMETER | About 47.5 mm |
| FLOWER DEPTH (HEIGHT) | About 40.7 mm |
| FLOWER LONGEVITY ON PLANT | About 7-10 days |
| PERSISTENT OR SELF-CLEANING? | Self-cleaning |
| PETAL TEXTURE, UPPER SURFACE | Smooth |
| PETAL TEXTURE, LOWER SURFACE | Smooth |
| TUBE TEXTURE, | Pubescent |
| PETAL ARRANGEMENT | Single whorl |
| PETAL NUMBER | 5 |
| PETALS FUSED? | Fused |
| PETAL SHAPE | Spatulate |
| PETAL MARGIN | Entire, weakly undulated |
| PETAL TIP | Cuspidate |
| PETAL BASE | Fused |
| PETAL LENGTH | About 20.3 mm |
| PETAL WIDTH | About 20.9 mm |
| PETAL COLOR, WHEN OPENING, UPPER SIDE | Near Bicolor, 86A and RHS NN155C |
| PETAL COLOR, WHEN OPENING, LOWER SIDE | Near Bicolor, N81B and RHS NN155C |
| PETAL COLOR, FULLY OPENED, UPPER SIDE | Near Bicolor, N81A and RHS NN155C |
| PETAL COLOR, FULLY OPENED, LOWER SIDE | Near Bicolor, 83C and RHS NN155C |
| PETAL COLOR, FADING TO | — |
| THROAT DIAMETER | About 9.7 mm |
| TUBE DIAMETER(PROXIMAL END) | About 2.6 mm |
| TUBE LENGTH | About 26.5 mm |
| THROAT COLOR(inside) | Near NN155A RHS 145B (Yellow Green) |
| TUBE COLOR(outside) | Near NN155A RHS |
| SEPAL ARRANGEMENT | Single whorl |
| NUMBER OF SEPALS | 5 |
| SEPAL SHAPE | Narrow elliptic |
| SEPAL MARGIN | Entire |
| SEPAL TIP | Obtuse |
| SEPAL BASE | Fused |

TABLE 1-continued

| PLANT VARIETY DESCRIPTION | |
|---|---|
| CHARACTERISTIC | APPLICATION VARIETY Sunpetu 101 |
| SEPAL LENGTH | About 15.9 mm |
| SEPAL WIDTH | About 2.4 mm |
| SEPAL COLOR, IMMATURE, UPPER SIDE | Near 137B RHS |
| SEPAL COLOR, IMMATURE, UNDER SIDE | Near 137D RHS |
| SEPAL COLOR, MATURE, UPPER SIDE | Near 137B RHS |
| SEPAL COLOR, MATURE, UNDER SIDE | Near 137D RHS |
| CALYX SHAPE | Tubular, star shape |
| CALYX LENGTH | About 11.7 mm |
| CALYX DIAMETER | About 21.8 mm |
| PEDUNCLE LENGTH | About 21.2 mm |
| PEDUNCLE DIAMETER | About 1.0 mm |
| PEDUNCLE ANGLE | Upright to outward |
| PEDUNCLE TEXTURE | Pubescent |
| PEDUNCLE COLOR | Near 144A RHS |
| STAMEN NUMBER | 5 |
| STAMEN LENGTH | About 16.2-21.1 mm |
| ANTHER SHAPE | Ellipsoidal |
| ANTHER SIZE | About 2.6 × 1.6 mm |
| ANTHER COLOR | Near 156D RHS |
| AMOUNT OF POLLEN | Moderate |
| POLLEN COLOR | Near 157A RHS |
| PISTIL NUMBER | 1 |
| PISTIL LENGTH | About 19.6 mm |
| STIGMA SHAPE | Transversely ellipsoidal |
| STIGMA COLOR | Near 90B RHS |
| STYLE COLOR | Near 144D RHS |
| OVARY COLOR | Near 144B RHS |
| OTHER FLOWER CHARACTERISTICS | — |
| QUANTITY OF SEEDS | Seed production has not been observed. |
| ROOT STRUCTURES such as BULBS, CORMS or RHIZOMES? | Fibrous root |
| LOW TEMPERATURE TOLERANCE | Good |
| HIGH TEMPERATURE TOLERANCE | Good |
| DISEASE RESISTANCE AND/OR SUSCEPTIBILITY | — |
| RESISTANCE OF PESTS AND/OR SUSCEPTIBILITY | — |

This new variety of *Petunia* plant having the above botanical characteristics is suitable for flower bedding and potting, particularly in hanging pots or planters.

It is claimed:

1. A new and distinct variety of *Petunia* plant named 'Sunpetu 101', substantially as herein illustrated and described.

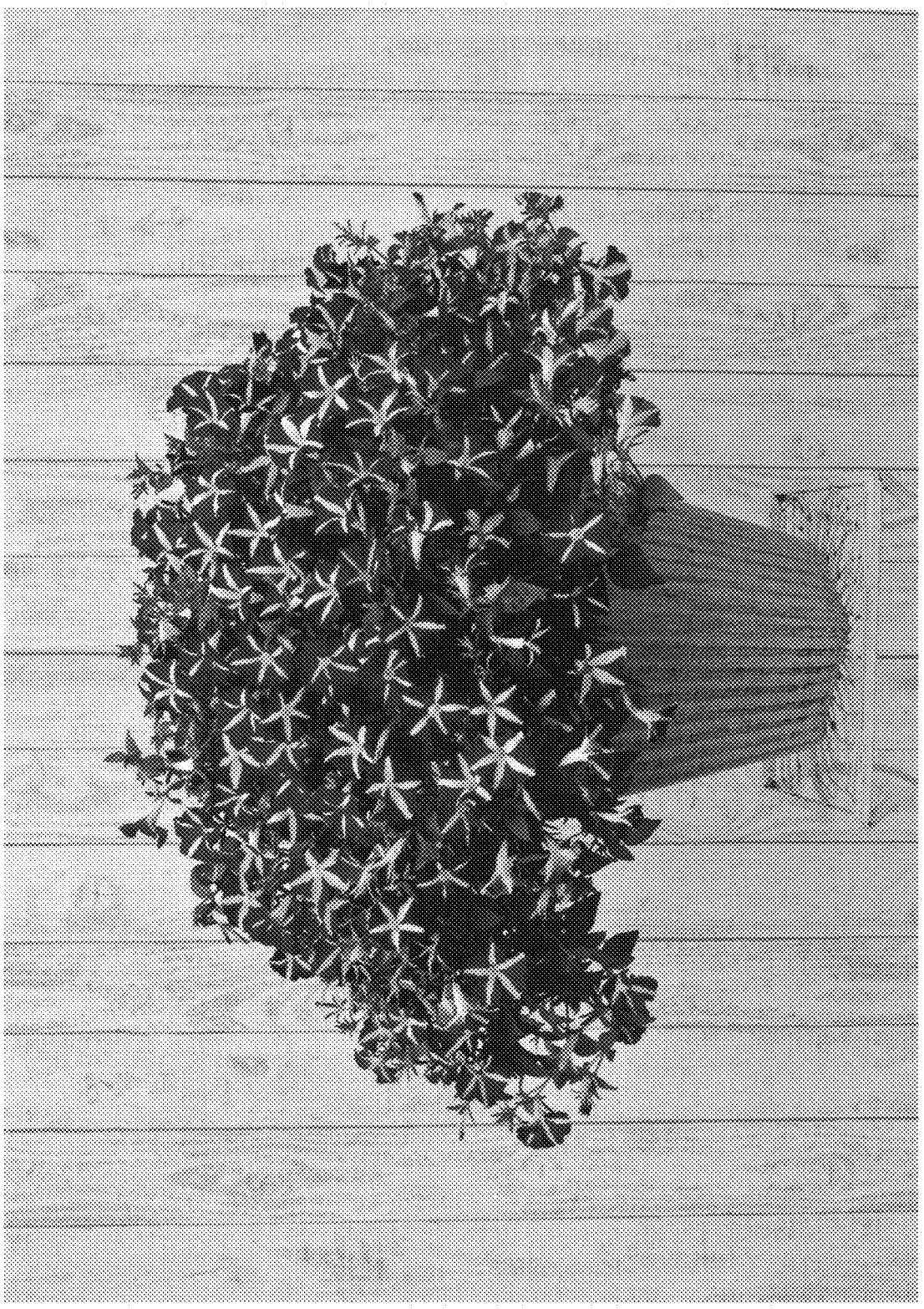

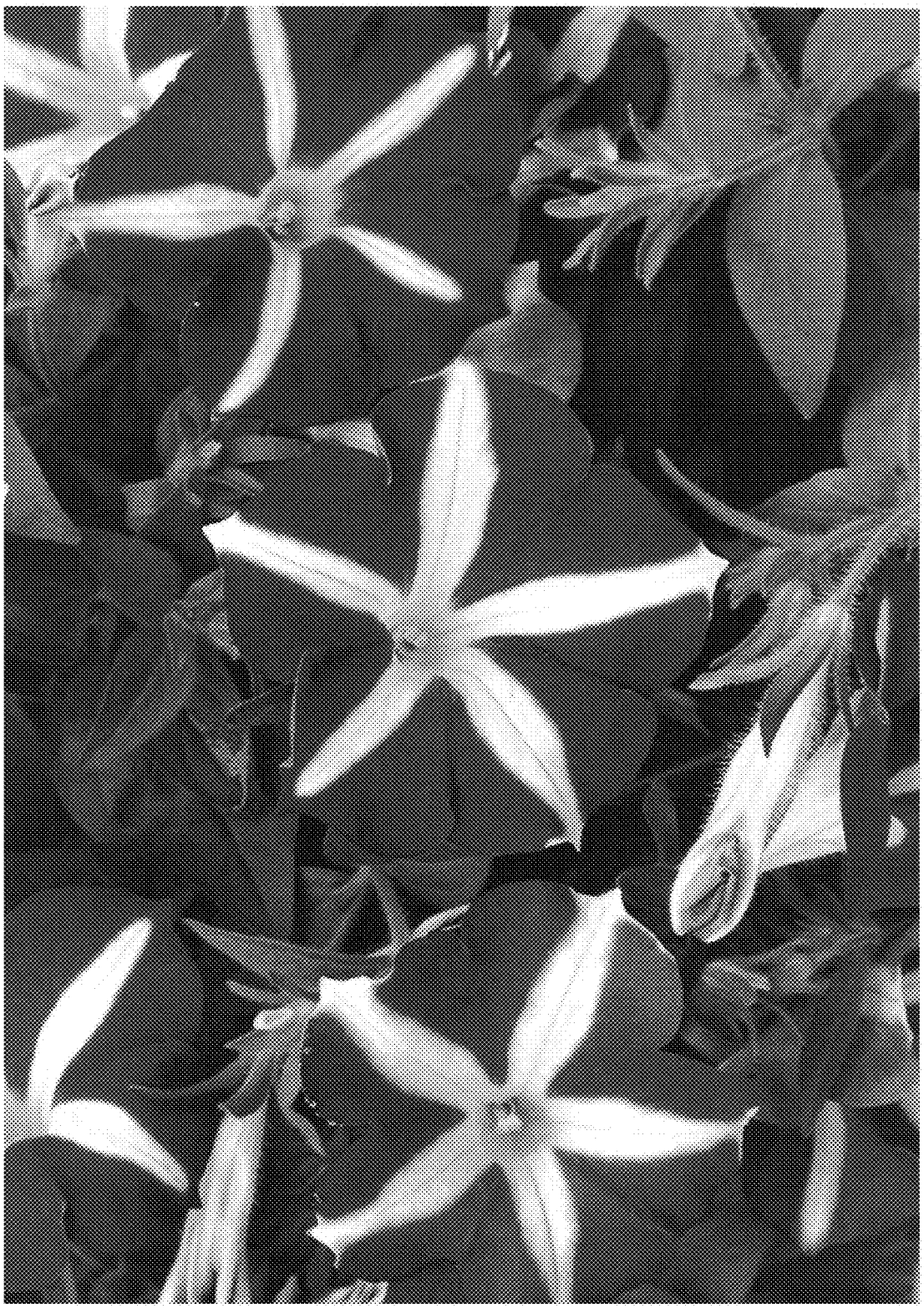

* * * * *